United States Patent
Bourdon et al.

(10) Patent No.: US 10,307,512 B2
(45) Date of Patent: Jun. 4, 2019

(54) PROCESS FOR PREPARING HYDROGELS

(71) Applicant: Teoxane, Geneva (CH)

(72) Inventors: Francois Bourdon, Gaillard (FR); Stephane Meunier, Thoiry (FR)

(73) Assignee: TEOXANE, Geneva (CH)

( * ) Notice: Subject to any disclaimer, the term of this patent is extended or adjusted under 35 U.S.C. 154(b) by 30 days.

(21) Appl. No.: 15/536,039

(22) PCT Filed: Dec. 15, 2015

(86) PCT No.: PCT/EP2015/079889
§ 371 (c)(1),
(2) Date: Jun. 14, 2017

(87) PCT Pub. No.: WO2016/096920
PCT Pub. Date: Jun. 23, 2016

(65) Prior Publication Data
US 2017/0354761 A1    Dec. 14, 2017

(30) Foreign Application Priority Data
Dec. 15, 2014 (FR) ..................... 14 62401

(51) Int. Cl.
C08B 37/00 (2006.01)
A61L 27/52 (2006.01)
A61L 27/20 (2006.01)
A61K 8/73 (2006.01)
A61Q 19/08 (2006.01)
A61K 8/04 (2006.01)
A61K 31/728 (2006.01)
C08B 37/08 (2006.01)
C08L 5/08 (2006.01)
A61K 8/24 (2006.01)
A61K 9/06 (2006.01)
A61Q 11/00 (2006.01)

(52) U.S. Cl.
CPC .............. *A61L 27/52* (2013.01); *A61K 8/042* (2013.01); *A61K 8/24* (2013.01); *A61K 8/735* (2013.01); *A61K 9/06* (2013.01); *A61K 31/728* (2013.01); *A61L 27/20* (2013.01); *A61Q 11/00* (2013.01); *A61Q 19/08* (2013.01); *C08B 37/0063* (2013.01); *C08B 37/0072* (2013.01); *C08L 5/08* (2013.01); *A61K 2800/91* (2013.01); *A61L 2400/06* (2013.01); *A61L 2430/16* (2013.01); *A61L 2430/24* (2013.01)

(58) Field of Classification Search
CPC ................................. C08B 37/0072
See application file for complete search history.

(56) References Cited

U.S. PATENT DOCUMENTS

| 5,783,691 A | 7/1998 | Malson et al. |
| 2006/0105022 A1 | 5/2006 | Yokokawa et al. |
| 2007/0036745 A1 | 2/2007 | Leshchiner et al. |
| 2008/0139796 A1 | 6/2008 | Yagi et al. |
| 2013/0123210 A1* | 5/2013 | Liu ............... A61K 8/676 514/54 |

FOREIGN PATENT DOCUMENTS

| EP | 1992364 A1 | 11/2008 | |
| FR | 2945293 A1 | 11/2010 | |
| FR | 2997085 A1 | 4/2014 | |
| JP | H08157378 A | 6/1996 | |
| WO | WO03/021039 | * 3/2003 | ............ D21H 19/42 |
| WO | 2006056204 A1 | 6/2006 | |
| WO | 2008090583 A1 | 7/2008 | |
| WO | 2009047346 A1 | 4/2009 | |
| WO | WO2014/181147 | * 11/2014 | ............... A61K 8/24 |

OTHER PUBLICATIONS

Sigma-Aldrich catalog entry for 1,4-butanediol diglycidyl ether, downloaded from https://www.sigmaaldrich.com/catalog/product/aldrich/220892?lang=en&region=US (Year: 2018).*
International Search Report for PCT/EP2015/079889 dated Mar. 23, 2016 (3 pages).
Lack et al., "High-resolution nuclear magnetic resonance spectroscopy studies of polysaccharides crosslinked by sodium trimetaphosphate: a proposal for the reaction mechanism" ScienceDirect Carbohydrate Research 342 (2007) 943-953 (11 pages).
Dulong et al., "Pullulan—STMP hydrogels: a way to correlate crosslinking mechanism, structure and onysicochemical properties" Polym. Bull. Published online: Jan. 20, 2011 (12 pages).

* cited by examiner

*Primary Examiner* — Eric Olson
(74) *Attorney, Agent, or Firm* — Shumaker, Loop & Kendrick, LLP

(57) ABSTRACT

The present invention relates to a process for preparing a crosslinked gel of at least one polysaccharide or a salt thereof, comprising at least the steps consisting in: a) providing a solution formed from an aqueous medium comprising at least said polysaccharide(s) or a salt thereof in a non-crosslinked form, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt; b) crosslinking the solution from step a) and, where appropriate; c) recovering said crosslinked gel formed.

19 Claims, No Drawings

PROCESS FOR PREPARING HYDROGELS

TECHNICAL FIELD AND BACKGROUND OF THE INVENTION

The present invention is directed towards proposing a process for preparing hydrogels based on a crosslinked polysaccharide, preferably hyaluronic acid, or a salt thereof.

Hyaluronic acid, which is naturally present in the skin, is known for its viscoelastic properties and its immense water-absorbing capacity. Its properties contribute largely to the elasticity of the skin.

It is precisely with regard to these properties that this compound has been exploited for more than 10 years in numerous applications falling within the medical and cosmetic fields, such as cosmetic surgery, dental surgery, articular viscosupplementation or ophthalmology.

Thus, hyaluronic acid is especially used for filling wrinkles and for attenuating, or even eliminating, local collapse of the structure of the dermis in the form of a wrinkle, generally via direct injection into the dermis, at the site of the wrinkle concerned.

In point of fact, hyaluronic acid is used essentially in the form of a crosslinked gel, given the increased resistance of this particular form to heat-mediated degradation, and thus to sterilization.

These crosslinked hyaluronic acid gels may be obtained via various preparation processes. In general, these processes require two main steps, the first consisting in hydrating the hyaluronic acid to convert it into an aqueous gel and the second directed towards crosslinking said aqueous gel in the presence of an agent that is capable of inducing its crosslinking (also known as a "crosslinking agent").

As illustrations of these processes, mention may be made especially of those described in documents US 2006/0 105 022, WO 2006/056 204 or US 2007/0 036 745.

For obvious reasons, improving the mechanical properties of hydrogels, based on a crosslinked polysaccharide, this objective being liable to proceed via improving the processes for preparing these hydrogels, is an ongoing aim.

In this respect, FR 2 997 085 describes a process including the presence of an alkaline halide salt, especially of NaCl, during the implementation of the crosslinking reaction. This alkaline halide salt makes it possible to improve the rheo logical properties of the crosslinked gel.

SUMMARY

The present invention is directed towards proposing a process for obtaining crosslinked gels that have even more advantageous mechanical properties.

Contrary to all expectation, the inventors have found that performing the step of crosslinking the polysaccharide, especially hyaluronic acid, in the presence of a conventional crosslinking agent and also of a particular compound, gives access to a crosslinked gel that is particularly advantageous in terms of mechanical properties and of resistance to heat-mediated degradation (sterilization) and to oxidative stress (by incubation with $H_2O_2$), when compared with the gels obtained via conventional processes.

DETAILED DESCRIPTION

Thus, according to a first of its aspects, the present invention relates to a process for preparing a crosslinked gel of at least one polysaccharide or a salt thereof, comprising at least the steps consisting in:

a) providing a solution (or mixture) formed from an aqueous medium comprising at least said polysaccharide(s) or a salt thereof in a non-crosslinked form, at least one difunctional or multifunctional epoxide crosslinking agent chosen from butanediol diglycidyl ether, diepoxy-octane or 1,2-bis-(2,3-epoxypropyl)-2,3-ethylene, mixtures thereof, and at least one phosphate salt;

b) crosslinking the solution from step a) and, where appropriate;

c) recovering said crosslinked gel formed.

Preferably, the crosslinking step b) is performed at room temperature.

More precisely, and as emerges from the examples below, the invention results from the unexpected observation by the inventors that the presence of a phosphate salt, during the implementation of the crosslinking reaction, makes it possible to significantly improve:

the rheological properties of the crosslinked gel obtained; and the properties of resistance to heat-mediated degradation (sterilization) and to oxidative stress (incubation with $H_2O_2$) of the crosslinked gel obtained.

What is more, and even more unexpectedly, the inventors have observed that the presence of a phosphate salt leads to effective crosslinking of the polysaccharide with very low amounts of crosslinking agent which, in the absence of said phosphate salt, do not make it possible to achieve effective crosslinking of the polysaccharide. This emerges especially from Example 1 below.

The presence of at least one phosphate salt during the crosslinking reaction even leads to a synergistic effect since the rheological properties of the crosslinked gel obtained cannot be reproduced with crosslinked gels whose crosslinking is performed sequentially, namely in the presence of a difunctional or multifunctional epoxide crosslinking agent and then of a phosphate salt, or vice versa. This emerges especially from Example 4 below.

From these observations, it follows that a process in accordance with the invention is advantageous in that it can give access to a satisfactory crosslinked gel, especially for filling wrinkles, by using reduced amounts of difunctional or multifunctional epoxide crosslinking agent, but which, on the other hand, has rheological properties at least equivalent to those shown by a crosslinked gel obtained via a standard crosslinking process using larger amounts of difunctional or multifunctional epoxide crosslinking agent.

A process in accordance with the invention thus makes it possible to limit the amount of difunctional or multifunctional epoxide crosslinking agent to be introduced for implementing the crosslinking reaction, and thus (1) to limit the potential amount of residual difunctional or multifunctional epoxide crosslinking agent after the crosslinking reaction, which a person skilled in the art is nowadays seeking to dispense with as much as possible, especially by means of subsequent purification steps, and (2) to reduce the degree of modification of the crosslinked polysaccharide, i.e. to come as close as possible to the polysaccharide in its natural, non-crosslinked form. This emerges especially from Example 1 below.

The use of a phosphate salt in the presence of a polysaccharide has already been considered for the purposes of crosslinking or functionalizing said polysaccharide (Lack et al., 2007, Carbohydrate Research, 342: 943; Dulong et al., 2011, Springer, Polym. Bull.; WO 2008/090 583, WO 2009/047 346 or U.S. Pat. No. 5,783,691). However, none of these documents describes the unexpected effect of a phosphate salt as a "booster" in the case of crosslinking between a polysaccharide and a difunctional or multifunctional epoxide crosslinking agent.

All the abovementioned advantages in connection with a process according to the present invention are all the more unexpected since no reaction for attaching the phosphate salt to the polysaccharide has been demonstrated. This emerges more particularly from Example 1 below.

According to a particular embodiment, a process of the invention may also comprise at least one step d) of homogenizing the solution (or mixture) from step a), this step being performed prior to and/or simultaneously with the crosslinking step b), preferably prior to the crosslinking step b).

Advantageously, the crosslinked gel obtained after performing a process in accordance with the invention is a predominantly elastic viscoelastic gel, i.e. having a reduced capacity, or even having no capacity, for flowing in the absence of constraints other than its own weight.

According to another of its aspects, the present invention relates to an injectable sterile dermatological composition comprising, in a physiologically acceptable medium, at least one crosslinked gel obtained by performing a process according to the present invention.

According to yet another of its aspects, the present invention relates to a cosmetic or dermatological composition comprising at least one crosslinked gel obtained by performing a process according to the present invention.

According to another of its aspects, the present invention relates to a kit comprising:
- packaging containing at least one dose of a crosslinked gel obtained by performing a process according to the present invention or of a composition as defined above; and
- a device for injection into or through the skin or a skin microperforation device, intended for administering said dose.

According to another of its aspects, the present invention relates to use of a crosslinked gel obtained by performing a process according to the present invention, for filling skin volume defects, and especially for filling wrinkles.

The present invention also relates to a crosslinked gel obtained by performing a process according to the present invention, for its use for treating gingival deficiencies, in particular periodontal diseases and associated disorders.

The present invention also relates to the use of a crosslinked gel obtained by performing a process according to the present invention for treating gingival deficiencies, in particular periodontal diseases and associated disorders.

The present invention also relates to a method for treating gingival deficiencies, in particular periodontal diseases and associated disorders, comprising a step for injecting in the gingiva of a patient a crosslinked gel obtained by performing a process according to the present invention.

The term "periodontal disease" is a generic name used to describe inflammatory diseases of the periodontium, the surrounding tissues and the tissues for fixing the teeth in the jaw. The periodontium consists of cement, periodontal ligaments and gum, which comprises alveolar bone and the soft tissues covering it. Periodontal disease is the main cause of tooth loss in the adult population (Anderson's Pathology, page 2000, John M. Kissane ed., $9^{th}$ ed. (1992)).

The present invention also relates to a crosslinked gel obtained by performing a process according to the present invention, for its use for articular viscosupplementation.

The present invention also concerns the use of a crosslinked gel obtained by performing a process according to the present invention for treating articular viscosupplementation.

The present invention also relates to a method for treating athrosis, comprising a step for injecting in the articulation of a patient concerned by arthrosis a crosslinked gel obtained by performing a process according to the present invention.

The present invention also relates to a crosslinked gel obtained by performing a process according to the present invention, for its use for treating ophthalmic disorders, especially for extracting cataracts and for inserting and removing intraocular lenses (IOL).

The present invention also concerns the use of a crosslinked gel obtained by performing a process according to the present invention for treating ophthalmic disorders, especially for extracting cataracts and for inserting and removing intraocular lenses (IOL).

The present invention also relates to a method for treating ophthalmic disorders, especially for extracting cataracts and for inserting and removing intraocular lenses (IOL), comprising a step for injecting in the eye of a patient a crosslinked gel obtained by performing a process according to the present invention.

For the purposes of the present invention, the term "skin" includes the skin of the face, the neck, the neckline, the hands, the scalp, the abdomen and/or the legs, but also the lips.

Polysaccharide

The term "polysaccharide" means any polymer consisting of several saccharides linked together via O-oside linkages and having the general formula: —[Cx(H2O)y)]n-.

For the purposes of the present invention, the term "non-crosslinked" is intended to denote an aqueous gel of non-crosslinked or unconverted polysaccharides, i.e. a solution of polysaccharides in which the chains of the polymer(s) are not connected together via strong or covalent bonds.

A polysaccharide in accordance with the invention is more particularly selected with regard to the properties that it is desired to be manifested by the crosslinked gel obtained according to the invention. More particularly, such a polysaccharide should have good biocompatibility.

Also, a polysaccharide according to the invention should have good stability over time, especially after crosslinking, given its intended use, namely especially for filling skin volume defects, and especially for filling wrinkles.

A polysaccharide or polysaccharide salt according to the invention is thus physiologically acceptable and may be of natural or synthetic origin.

The polysaccharides that are suitable for use in the invention may be chosen especially from chondroitin sulfate, keratan, keratan sulfate, heparin, heparin sulfate, xanthan, carrageenans, hyaluronic acid (HA), chitosan, cellulose and derivatives thereof, alginate, starch, dextran, pullulan, galactomannan and biologically acceptable salts thereof.

The polysaccharide salts in accordance with the invention are more particularly chosen from physiologically acceptable salts, such as the sodium salt, the potassium salt, the zinc salt, the silver salt, and mixtures thereof, preferably the sodium salt.

Preferably a polysaccharide or polysaccharide salt according to the invention, or even hyaluronic acid (HA), has a high molecular weight, preferably an average molecular weight of greater than or equal to 50 000 Da, or even greater than 3 MDa depending on the application under consideration.

Advantageously, a polysaccharide or polysaccharide salt according to the invention, or even hyaluronic acid, may have an average molecular weight ranging from 50 000 to 10 000 000 daltons and preferably from 500 000 to 4 000 000 daltons.

A particularly preferred polysaccharide is hyaluronic acid (HA) or a salt thereof, preferably sodium hyaluronate (NaHA).

Difunctional or Multifunctional Epoxide Crosslinking Agent

The term "difunctional or multifunctional epoxide crosslinking agent" means any compound that is capable of inducing crosslinking between the various polysaccharide chains and comprising at least one difunctional or multifunctional epoxide group.

The choice of this crosslinking agent with regard to the polysaccharide to be crosslinked clearly falls within the competence of a person skilled in the art.

As crosslinking agents in accordance with the present invention, mention may be made especially of difunctional or multifunctional epoxide crosslinking agents chosen from butanediol diglycidyl ether (BDDE), diepoxyoctane, 1,2-bis (2,3-epoxypropyl)-2,3-ethylene, and mixtures thereof.

Preferably, a crosslinking agent in accordance with the invention is butanediol diglycidyl ether (BDDE).

Adjusting the amount of difunctional or multifunctional epoxide crosslinking agent to perform the crosslinking reaction also falls within the competence of a person skilled in the art.

Advantageously, the "number of moles of difunctional or multifunctional epoxide crosslinking agent(s)/total number of moles of polysaccharide units" molar ratio in a solution according to step a) may be between 0.005 and 1, preferably between 0.01 and 0.25.

The total number of moles of polysaccharide units may preferably be the total number of moles of disaccharide units forming the hyaluronic acid monomer.

Phosphate Salt

As indicated above, the inventors have observed, unexpectedly, that, besides the difunctional or multifunctional epoxide crosslinking agent, the additional presence of at least one phosphate salt for the implementation of the crosslinking step leads to a significant improvement in properties, in terms of rheology and of resistance to heat-mediated degradation (sterilization) and to oxidative stress (by incubation with $H_2O_2$), manifested by a crosslinked gel obtained after the process according to the invention.

A phosphate salt according to the invention may be chosen from the sodium salts, the potassium salts, the lithium salts, the caesium salts and the silver salts, and mixtures thereof, preferably a sodium salt.

Advantageously, a phosphate salt according to the invention may be chosen from sodium phosphate (SP), sodium triphosphate (STPP) and sodium trimetaphosphate (STMP), and mixtures thereof, preferably sodium trimetaphosphate.

Advantageously, the "number of moles of phosphate salt(s)/total number of moles of polysaccharide units" molar ratio in a solution according to step a) may be between 0.005 and 1, preferably between 0.01 and 0.25.

In this case also, the total number of moles of polysaccharide units may preferably be the total number of moles of disaccharide units forming the hyaluronic acid monomer.

Process According to the Invention

A process of the invention requires, in a first stage, a solution formed from an aqueous medium (or aqueous gel) comprising at least one polysaccharide, or a salt thereof, in a non-crosslinked form.

The solution under consideration in step a) of a process according to the present invention may be obtained beforehand by placing in contact, in a suitable container:
 (i) an aqueous medium;
 (ii) at least one polysaccharide, or a salt thereof, in a non-crosslinked form;
 (iii) at least one difunctional or multifunctional epoxide crosslinking agent; and
 (iv) at least one phosphate salt,
the order of addition of compounds (i) to (iv) to the container being irrelevant.

According to a first embodiment variant, the solution under consideration in step a) of a process according to the present invention is obtained beforehand by placing in contact, in a suitable container:
 (i) an aqueous medium;
 (ii) at least one polysaccharide, or a salt thereof, in a non-crosslinked form; followed by addition
 (iii) of at least one difunctional or multifunctional epoxide crosslinking agent; and
 (iv) at least one phosphate salt,
the order of addition of compounds (iii) and (iv) to the container being irrelevant, or even the addition of compounds (iii) and (iv) to the container advantageously being simultaneous.

The simultaneous addition of compounds (iii) and (iv) to the container involves a prior or parallel step of preparing a solution (known as the crosslinking solution) comprising at least the difunctional or multifunctional epoxide crosslinking agent(s) and the phosphate salt(s).

According to a second embodiment variant, the solution under consideration in step a) of a process according to the present invention is obtained beforehand by placing in contact, in a suitable container:
 (i) an aqueous medium;
 (ii) at least one difunctional or multifunctional epoxide crosslinking agent;
 (iii) at least one phosphate salt; followed by addition
 (iv) of at least one polysaccharide, or a salt thereof, in a non-crosslinked form,
the order of addition of compounds (i), (ii) and (iii) to the container being irrelevant, or even the addition of compounds (ii) and (iii) to the container advantageously being simultaneous.

The simultaneous addition of compounds (ii) and (iii) to the container involves a prior or parallel step of preparing a solution (known as the crosslinking solution) comprising at least the difunctional or multifunctional epoxide crosslinking agent(s) and the phosphate salt(s).

For the purposes of the present invention, the term "aqueous medium" means any liquid medium containing water and which has the property of dissolving a polysaccharide or a salt thereof.

The nature of the aqueous medium is more particularly conditioned with regard to the type of crosslinking envisaged, the type of crosslinking agent under consideration, but also the type of polysaccharide used.

In this respect, the aqueous medium that is liable to be suitable for use will be pH-adjusted according to the knowledge of a person skilled in the art.

Preferably, and especially given the difunctional or multifunctional epoxide crosslinking agent, the aqueous medium is preferably basic. Thus, and even more preferably, the aqueous medium has a basic pH, preferably greater than 11, or even greater than 12.

For example, in the case of using BDDE as difunctional or multifunctional epoxide crosslinking agent, a particularly preferred aqueous medium may be an alkaline medium, preferably sodium hydroxide (NaOH), more particularly a sodium hydroxide solution at a pH greater than 12.

Advantageously, this step of forming a solution according to step a) may be performed at room temperature, preferably at a temperature below 35° C. and better still at a temperature ranging from 15 to 25° C.

The formation of a solution as considered in step a) advantageously involves at least one homogenization, as indicated above. This step is illustrated by step d) of the process of the invention.

The aim of this operation is more particularly to hydrate and homogenize the polysaccharide fully in the aqueous medium, and thus to contribute towards optimizing the qualities of the expected crosslinked gel.

The aim of this operation is also to homogenize the difunctional or multifunctional epoxide crosslinking agent and the phosphate salt in the solution from step a), also contributing towards optimizing the qualities of the expected crosslinked gel.

The homogenization is considered as satisfactory when the solution obtained has a homogeneous colour, with no agglomerates and a uniform viscosity. It may advantageously be performed under mild operating conditions to prevent degradation of the polysaccharide chains.

This step is all the more important when the polysaccharide has a high molecular weight. Specifically, the hydration of such a compound then has a tendency to give rise to the formation of a solution of high viscosity within which the appearance of agglomerates is commonly observed.

Step d) of homogenizing the solution obtained in step a) is performed prior to and/or simultaneously with the crosslinking step b) described below, preferably prior to the crosslinking step b).

The duration of this homogenization step depends especially on the nature of the polysaccharide, and more particularly on its molecular weight, its concentration, the respective contents of the various compounds used, especially the amounts of polysaccharide(s) employed, the operating conditions within the aqueous medium and the homogenization device used.

Adjusting the appropriate homogenization time to obtain an aqueous polysaccharide gel that is sufficiently homogeneous falls within the general competence of a person skilled in the art.

The homogenization may also be broken down into several cycles, optionally with waiting times between the cycles, especially so as to assess the homogenization quality of the polysaccharide(s) in the aqueous medium.

Preferably, a homogenization step according to the present invention may take place over a total time of less than 200 minutes, preferably less than 150 minutes, or even between 5 and 100 minutes.

The solution from step a) is then subjected to suitable conditions for the crosslinking reaction.

This step is illustrated by step b) of the process of the invention.

The aim of the crosslinking is to create bridges between the chains of polysaccharides, and especially of hyaluronic acid, making it possible to obtain a solid and dense three-dimensional network from a viscous solution.

The first condition for inducing the implementation of the crosslinking reaction in a process according to the present invention lies in the presence, in the solution from step a) of at least one difunctional or multifunctional epoxide crosslinking agent and of at least one phosphate salt.

The operating conditions of the crosslinking reaction may depend especially on the nature of the polysaccharide, its molecular weight, the nature of the difunctional or multifunctional epoxide crosslinking agent and the aqueous medium.

According to a first embodiment variant, the crosslinking step b) is performed at room temperature.

Preferably, and according to this embodiment variant, the crosslinking step b) may be performed at a temperature below 35° C., preferably at a temperature ranging from 15 to 25° C. and better still from 19 to 23° C.

Crosslinking at room temperature involves crosslinking kinetics such that the crosslinking step b) can then preferably take place over a period of between 5 hours and 336 hours (i.e. 2 weeks), preferably between 20 hours and 150 hours and better still between 40 hours and 100 hours.

Faster crosslinking kinetics, i.e. less than 5 hours, may be acquired by placing a solution from step a) in contact with at least one stimulating element, other than the difunctional or multifunctional epoxide crosslinking agent and the phosphate salt. The stimulating element may be featured, for example, by heating, exposure to UV, exposure to microwaves, or even placing the solution from step a) in contact with a material of catalyst type.

The choice of such a stimulating element falls within the general knowledge of a person skilled in the art.

Thus, a stimulating element may consist of:
immersion of the container comprising the solution from step a) in a bath containing a hot fluid, for example whose temperature is greater than 40° C., preferably between 45 and 60° C.;
exposure of the latter to radiation of certain wavelengths of UV type, for example, to microwave radiation or to infrared radiation;
irradiation of the latter using ionizing rays, in the manner of the process described in document US 2008/0 139 796; and
enzymatic crosslinking;
addition of a catalyst and/or of a reaction intermediate, or even
combinations between the various abovementioned elements.

Preferably, and according to the embodiment variant in which the crosslinking step b) is performed in the presence of a stimulating element, said stimulating element consists of raising of the temperature of the solution from step a).

Advantageously, and according to this embodiment variant, the crosslinking step b) is performed at a temperature greater than 40° C., preferably greater than 50° C., more particularly between 45 and 60° C. and better still between 50 and 55° C.

The degree of crosslinking also depends on the crosslinking time imposed on the gels. The longer the time, the greater the crosslinking will be, with, however, an optimum that should not be exceeded.

Thus, in the case of crosslinking performed in the presence of a stimulating element, especially raising of the temperature as described above, the crosslinking step b) may advantageously be performed over a period ranging from 30 to 300 minutes, preferentially from 100 to 240 minutes.

According to a particularly preferred embodiment considering the use of a stimulating element, especially featured by raising of the temperature as described above, the crosslinking step b) is performed at a temperature of about 50 to 55° C., for a period of 100 to 240 minutes.

Advantageously, the crosslinking conditions are adjusted to obtain a degree of crosslinking such that the gel formed is a viscoelastic gel, or even predominantly elastic.

The crosslinking may be stopped prior to, simultaneously with or subsequent to the step of recovering the gel c).

For example, the crosslinking may be stopped or may result from:
- neutralization of the pH;
- dilution of the crosslinked gel;
- stopping the operating conditions, for example stopping the radiation or the heating; and/or
- depletion of difunctional or multifunctional epoxide crosslinking agent.

According to a particularly preferred embodiment, the process according to the invention uses (i) sodium hyaluronate as polysaccharide in an alkaline medium, (ii) butanediol diglycidyl ether (BDDE) as difunctional or multifunctional epoxide crosslinking agent and (iii) sodium trimetaphosphate (STMP) as phosphate salt.

As indicated above, the advantageous effect associated with the presence of the phosphate salt allows the use of a reduced amount of difunctional or multifunctional epoxide crosslinking agent, when compared with the conventional processes, while at the same time maintaining satisfactory mechanical properties and satisfactory resistance to heat-mediated degradation and to oxidative stress for the crosslinked gels obtained after performing the process according to the invention.

Thus, according to this particular embodiment, the crosslinked polysaccharide(s) included in a crosslinked gel obtained by performing a process according to the invention may have a degree of modification of less than 10%, preferably between 0.1% and 5%, better still between 0.4% and 2.5%, or even between 0.7% and 1.6%, while at the same time remaining satisfactory as regards the mechanical properties and the resistance to heat-mediated degradation and to oxidative stress.

For the purposes of the present invention, the term "degree of modification" is intended to denote the ratio between the number of moles of crosslinking agent attached to the polysaccharide and the number of moles of polysaccharide forming said crosslinked gel. This magnitude may especially be measured by 1H NMR analysis of the crosslinked gel, as described in Example 1 below.

The term "number of moles of hyaluronic acid" means the number of moles of repeating disaccharide units of hyaluronic acid, the disaccharide unit being composed of D-glucuronic acid and D-N-acetylglucosamine linked together via alternating beta-1,4 and beta-1,3 glycoside linkages.

In addition, and as emerges from Example 1 below, the phosphate salt in a process according to the invention is also advantageous in that no additional modification of the polysaccharide associated with this phosphate salt has been identified.

Also, a crosslinked gel obtained by performing a process according to the present invention may have an elastic modulus (G') of between 20 and 1000 Pa, preferably between 35 Pa and 400 Pa, associated with a phase angle (δ) of less than 45°.

These parameters may especially be measured by means of the protocols described below.

According to a particular embodiment, and in order to further improve the qualities of the implant, a process according to the present invention may also comprise a step e) that consists in adding at least one non-crosslinked polysaccharide, preferably non-crosslinked hyaluronic acid, this step e) being performed prior to, simultaneously with or subsequent to the recovery step c), but necessarily after the crosslinking step b).

Thus, a crosslinked gel obtained by performing a process according to the present invention may also comprise a non-crosslinked polysaccharide, preferably non-crosslinked hyaluronic acid.

Preferably, step e), when it is present in a process according to the invention, is performed subsequent to the recovery step c).

The non-crosslinked polysaccharide, preferably non-crosslinked hyaluronic acid, may have the abovementioned characteristics.

According to yet another particular embodiment, a process according to the present invention may also comprise a step f) that consists in adding at least one anaesthetic, this step f) preferably being performed subsequent to the crosslinking step b), or even subsequent to the purification step defined below when said step is performed.

The choice and amount of anaesthetic are adjusted so as not to run any risk of incompatibility with the other compounds used in a crosslinked gel according to the invention, and especially with the polysaccharide and more particularly with hyaluronic acid, and so as to be compatible with the uses under consideration.

These adjustments fall within the general competence of a person skilled in the art.

An anaesthetic that may be used in the present invention may thus be chosen from ambucaine, amolanone, amylocaine, articaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquine, dimethocaine, diperodone, dycyclonine, ecgonidine, ecgonine, ethyl chloride, etidocaine, beta-eucaine, euprocine, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, paraparacaine, propipocaine, propoxycaine, pseudococaine, pyrrocaine, ropivacaine, salicyl alcohol, tetracaine, tolycaine, trimecaine and zolamine, or a salt thereof.

Preferably, the anaesthetic may be lidocaine and/or mepivacaine, and better still lidocaine hydrochloride.

According to yet another particular embodiment, a process according to the present invention may also comprise a step g) that consists in adding at least one additional active agent other than the compounds described previously, this step g) being performed prior to, simultaneously with and/or subsequent to the crosslinking step b), preferably subsequent to step b).

The choice and the amount of additional active agent are adjusted so as not to run the risk of incompatibility with the other compounds used in a crosslinked gel according to the invention, and especially with the polysaccharide and more particularly with hyaluronic acid, and so as to be compatible with the uses under consideration.

These adjustments fall within the general competence of a person skilled in the art.

Among the additional active agents that may be used in the present invention, mention may be made of antioxidants, amino acids, vitamins, minerals, nucleic acids, coenzymes, adrenalin derivatives, and a mixture thereof, said additional compounds under consideration being different from those indicated previously.

According to yet another particular embodiment, a process of the invention may be performed at least partly in a specific container with a deformable wall, for instance in a bag, especially that defined in document FR 2 945 293.

The crosslinked gel obtained after the process of the invention as described previously may be not directly injectable, especially with regard to its excessively high concentration of polysaccharide and/or the possible presence of residues of difunctional or multifunctional epoxide crosslinking agent, or alternatively of its physiological and/or pH conditions that are incompatible with use in the fields of application under consideration above.

In addition, the gel obtained after the process of the invention may especially have a rigidity that is too high to be injected in unmodified form into a patient.

Consequently, several additional steps, known to those skilled in the art, may be performed to obtain an injectable hydrogel.

More particularly, a step of neutralization and dilution of this gel may be required in order to give it its implant qualities. These steps make it possible to bring the cross-linked gel to a physiologically acceptable salt concentration and a physiologically acceptable pH.

The chains of the polysaccharide network are then stretched and hydrated, whereas the pH is brought to a value close to neutrality.

These steps clearly fall within the general competence of a person skilled in the art.

For further improved purity, especially to remove the residues of crosslinking agent(s) not attached to the polysaccharide(s), at least one purification step may also be performed.

Advantageously, this purification step may be performed via one or more dialysis baths.

Finally, the hydrogel thus obtained may be loaded into syringes under control-atmosphere conditions, said syringes then possibly undergoing a sterilization step, preferably thermally.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

The examples that follow are presented as non-limiting illustrations of the invention.

For each of the examples below, unless otherwise indicated, the percentages expressed are mass percentages.

Protocols

1) Procedure for Preparing a Crosslinked Hyaluronic Acid Gel

The procedure for preparing all the gels described in the examples below is as follows:

a) 10 g of NaHA are introduced into aqueous 1% sodium hydroxide solution, so as to obtain a homogeneous final solution (i.e. after step c) below) containing 12% NaHA, b) the crosslinking solution (=BDDE diluted to 20% in aqueous 1% sodium hydroxide solution, where appropriate in the presence of a compound A whose nature and amount are specified in each of the examples) is added to the mixture from step a). The amount of this solution incorporated is adjusted according to the desired molar ratios $R_{BDDE}=n_{BDDE}/n_{HA}$, and $R_A=n_A/n_{HA}$, as indicated in each of the examples, c) the mixture thus formed (i.e. obtained after step b)) is homogenized until the HA has totally dissolved (i.e. until no more agglomerate is present and a uniform colour is obtained), d) the homogeneous mixture obtained after step c) is crosslinked under the conditions described in each of the examples, e) after the crosslinking reaction, the material obtained is neutralized by adding HCl and diluted in pH 7.3 phosphate-buffered saline solution so as to obtain a hydrogel with the desired concentration of HA (=[HA] in mg/g, as specified in each of the examples), f) the hydrogel obtained is then purified by dialysis, according to the knowledge of a person skilled in the art, g) according to the examples, a solution of non-cross-linked HA is optionally incorporated and homogenized with the purified hydrogel of crosslinked HA obtained after step f) (expressed as % $HA_{non\text{-}crosslinked}/HA_{non\text{-}crosslinked+crosslinked}$, as specified in each of the examples), and h) the hydrogel is then introduced into syringes which are then sterilized in an autoclave (humid heat) at $T°\geq 121°$ C., so as to obtain an F0>15 (sterilizing value).

2) Viscoelastic Properties of the Gels Tested (i.e. Elastic Modulus G', Phase Angle δ, Compression Strength, Injection Force and Resistance to Degradation)

The viscoelastic properties of the gels are characterized in oscillatory rheology with deformation sweep, by measuring their elastic modulus G' (in Pa) and their phase angle δ (°), measured at 1 Hz for a stress of 5 Pa.

More precisely, these measurements are performed at 25° C. at a frequency of 1 Hz, with stress sweep using a Thermo Haake RS6000 rheometer with a 1°/35 mm diameter cone-plate geometry. G' and δ are recorded at an applied deformation stress of 5 Pa, i.e. in the viscoelastic range in which G' and δ remain stable (i.e. in the linear viscoelastic range).

The elastic modulus G', or storage modulus, measures the energy restored by the gel when it is subjected to a weak deformation. This magnitude may be imagined as being the stiffness of a spring.

The phase angle δ characterizes the degree of viscoelasticity of a material: it ranges between 0° for a 100% elastic material (all the deformation energy is restored by the material, i.e. it regains its initial shape) and 90° for a 100% viscous material (all the deformation energy is lost by the material, i.e. it flows and totally loses its initial shape). A cutaneous filling gel must be predominantly elastic to ensure its filling properties, i.e. δ must be <45°.

The compression strength is also measured, which corresponds to the average resistance of a gel when it is compressed between two plates. This magnitude is measured at 25° C., with 2.5 g of the gel placed between two circular plates 35 mm in diameter, with an initial gap of 10 mm. A compression of 70% of the height of the gap is applied at a rate of 0.1 mm/s. The compression strength is the integration over time of the force of resistance of the gel, and is thus expressed in N.s.

Finally, the injection force of the gels is measured in a syringe (1 mL long format) with 27G1/2 thin-walled needles, using a compression bench at a rate of descent of 12.5 mm/min.

The resistance to degradation is evaluated by the loss of elastic modulus G':

between before and after sterilization: this loss reflects heat-mediated degradation; and after sterilization, via degradation by incubation with $H_2O_2$: this loss reflects oxidative stress-mediated degradation (addition of 67 µl of 10% $H_2O_2$ solution to 2 g of gel followed by homogenization of the medium and then incubation for 24 hours at 37° C.). A measurement of the G' is taken before degradation and after the incubation for 24 hours at 37° C. in the presence of the $H_2O_2$ solution.

The G' is measured according to the abovementioned protocol. Since this G' results from the difference observed between two different moments, it is expressed as a percentage (%).

EXAMPLES

Example 1: Effect of a Phosphate Salt (STMP)

Three crosslinked hyaluronic acid gels 1b, 1c and 1d, crosslinked in the presence of different concentrations of sodium trimetaphosphate (SMTP) as compound A, are prepared according to the abovementioned procedure.

Gel 1a is free of STMP and is thus the control. It is also prepared according to the abovementioned procedure.

Table 1 below details the nature and amounts of the compounds used.

TABLE 1

| Parameters | $R_A$ | $R_{BDDE}$ | Crosslinking (in hours and in ° C.) | [HA] (mg/g) | $\%\frac{HA_{non-crosslinked}}{HA_{non-crosslinked\,+\,crosslinked}}$ |
|---|---|---|---|---|---|
| 1a (comparative) | 0 | 0.02 | 72 hours at 21 ± 2° C. | 23 | 10% |
| 1b (invention) | 0.03 | | (BDDE + STMP) | | |
| 1c (invention) | 0.06 | | | | |
| 1d (invention) | 0.09 | | | | |

The viscoelastic properties of gels 1a, 1b, 1c and 1d, measured according to the abovementioned protocols, are presented in Table 2 below.

TABLE 2

| | G' (in Pa) | δ (in °) | Compression strength (in N.s.) | Injection force (in N) |
|---|---|---|---|---|
| 1a (comparative) | 14 | 50.9 | 3.1 | 10.3 |
| 1b (invention) | 36 | 37.9 | 6.4 | 12.5 |
| 1c (invention) | 49 | 33.9 | 10.3 | 14.0 |
| 1d (invention) | 54 | 31.8 | 14.8 | 14.8 |

Gel 1a (control) is not suited to wrinkle-filling properties, since its phase angle δ is greater than 45°. In other words, the amount of crosslinking agent used is too low to obtain a crosslinked gel that is satisfactory as regards filling wrinkles.

On the other hand, gels 1b, 1c and 1d according to the present invention, although manufactured with the same amount of BDDE, have an angle δ of less than 45° and are thus satisfactory as regards filling wrinkles.

This effect is associated with the presence of STMP in the crosslinking system. What is more, it is observed that the more the amount of STMP increases, the more the elasticity part of the gel increases (i.e. decrease in δ), and the more the elastic modulus increases.

The increase in the amount of STMP between gels 1b, 1c and 1d according to the invention is also accompanied by an increase in the compression strength, thus revealing gels that are increasingly consistent and resistant to deformation.

The degradation-resistance properties of gels 1a, 1b, 1c and 1d, measured according to the abovementioned protocols, are presented in Table 3 below.

TABLE 3

| | Loss of G' after sterilization (%) | Loss of G' after oxidative stress (%) |
|---|---|---|
| 1a (comparative) | 43 | 89 |
| 1b (invention) | 14 | 65 |
| 1c (invention) | 9 | 65 |
| 1d (invention) | 19 | 48 |

Degree of Modification

Gels 1a and 1d are then evaluated as regards the degree of modification of hyaluronic acid. To this end, gels 1a and 1d are washed/precipitated using isopropanol. The solids obtained are dried and then dissolved in $D_2O$, and treated in the presence of hyaluronidase (type VI-S, Sigma, 3 kU) in 1 ml of $D_2O$ for degradation of the gel, so as to obtain a liquid matrix for analysis. Each homogeneous mixture obtained is then analysed by $^1H$ NMR.

Protocol for Measuring the Degree of Modification

Characterization of the degree of modification is performed by NMR spectroscopy. The degree of modification is obtained by applying the method developed by L. Nord et al. on samples of HA crosslinked with BDDE. The degree of modification is obtained by integrating the 1H NMR signal of the N-acetyl group (δ≈2 ppm) present in the HAs and a signal present in the crosslinking agent (two-CH2-groups, δ≈1.6 ppm). The ratio of the $$MoD = \frac{\left[\frac{Integral\ \delta_H\ 1.6}{4}\right]}{\left[\frac{Integral\ \delta_H\ 2.0}{3}\right]}$$

integrals of these two signals (crosslinking agent/NAc HA) corresponds to the degree of modification, after correction for the number of protons associated with each signal. The NMR analysis is performed on a Brüker Avance 1 spectrometer operating at 400 MHz ($^1H$).

The degrees of modification measured according to the above protocol for gels 1a and 1d are presented in the table below.

| GEL | Degree of modification |
|---|---|
| 1a (comparative) | 1.4% |
| 1d (invention) | 1.4% |

The same type of NMR analysis, but performed by phosphorus NMR ($^{31}P$ NMR) was performed. In this respect, the primary reference in $^{31}P$ NMR is aqueous 58% phosphoric acid (δ=0 ppm). This NMR analysis was performed on a Brüker Avance 1 spectrometer operating at 400 MHz ($^1H$) and 161.97 MHz (31P).

This analysis did not make it possible to reveal any attachment between the hyaluronic acid and a phosphorylated species derived from STMP.

The use of STMP in the presence of BDDE for performing the crosslinking reaction thus makes it possible to obtain crosslinked gels with satisfactory filling properties (mechanical properties and degradation resistance), such properties not being achievable, however, at the (nBDDE/nHA) molar ratio under consideration.

What is more, this effect of STMP occurs without increasing the degree of modification of the hyaluronic acid (HA).

Example 2: Confirmation of the Effect of a Phosphate Salt (STMP) on More Crosslinked Gels (i.e. $r_{BDDE}$ Greater than that of Example 1)

Three crosslinked hyaluronic acid gels 3b, 3c and 3d comprising the use of different concentrations of STMP as compound A are prepared according to the abovementioned procedure.

Gel 3a is free of STMP and is thus the control. It is also prepared according to the abovementioned procedure.

Table 4 below details the nature and amounts of the compounds used.

TABLE 4

| Parameters | $R_A$ | $R_{BDDE}$ | Crosslinking | [HA] (in mg/g) | $\% \frac{HA_{non\text{-}crosslinked}}{HA_{non\text{-}crosslinked\ +\ crosslinked}}$ |
|---|---|---|---|---|---|
| 3a (comparative) | 0 | 0.04 | 72 hours at 21 ± 2° C. (BDDE + STMP) | 18 | 10% |
| 3b (invention) | 0.02 | | | | |
| 3c (invention) | 0.04 | | | | |
| 3d (invention) | 0.06 | | | | |

The viscoelastic properties of gels 3a, 3b, 3c and 3d, measured according to the abovementioned protocols, are presented in Table 5 below.

TABLE 5

|  | G' (in Pa) | δ (in °) | Compression strength (in N.s.) | Injection force (in N) |
|---|---|---|---|---|
| 3a (comparative) | 96 | 16.2 | 16.4 | 12.4 |
| 3b (invention) | 107 | 15.3 | 17.4 | 11.3 |
| 3c (invention) | 117 | 14.0 | 18.0 | 10.8 |
| 3d (invention) | 197 | 10.8 | 20.2 | 9.5 |

Despite an HA concentration lower than that used in Example 1, gel 3a has satisfactory properties for the function of filling wrinkles, with a phase angle δ of less than 45° and far superior mechanical properties. This increase in the mechanical properties is associated with the amount of BDDE used ($R_{BDDE}$=0.04) which is higher than that of Example 1. The amount of BDDE crosslinking agent used in this gel 3a is thus satisfactory for obtaining a gel that is efficient as regards filling wrinkles.

Gels 3b, 3c and 3d according to the present invention have mechanical properties superior to those of the control gel 3a. This effect is associated with the presence of STMP in combination with the BDDE. The more the amount of STMP increases, the greater the increase in the mechanical properties. Thus, gel 3d has an elastic modulus G' more than 2 times higher than that of the control gel 3a.

The compression strength also increases with the amount of STMP used.

Finally, it is interesting to note that the injection force has a tendency to decrease with gels 3b, 3c and 3d according to the present invention; in all cases, the injection force is less than that obtained in Example 1, by virtue of the use of a lower concentration of HA. The improvement in the mechanical properties of a gel crosslinked according to a process according to the invention therefore does not take place at the expense of the injection force for a customary degree of crosslinking.

The degradation-resistance properties of gels 3a, 3b, 3c and 3d, measured according to the abovementioned protocols, are presented in Table 6 below.

TABLE 6

|  | Loss of G' after sterilization (%) | Loss of G' after oxidative stress (%) |
|---|---|---|
| 3a (comparative) | 40 | 73 |
| 3b (invention) | 15 | 47 |
| 3c (invention) | 18 | 45 |
| 3d (invention) | 15 | 30 |

Gels 3b, 3c and 3d crosslinked in the presence of STMP show a much higher resistance to degradation than that of gel 3a crosslinked without STMP. Gel 3d is the most resistant, with a minimal relative loss of elastic modulus G'.

Example 3: Effect of Different Phosphate Salts

Unlike sodium trimetaphosphate (STMP) which is cyclic, sodium triphosphate (STPP) is a linear phosphate salt. STMP and STPP are both triphosphates, and the amount tested is thus $R_A$=0.06, for comparison with gel 3d of Example 2, identical but with STMP.

Unlike STMP and STPP which are triphosphates, sodium phosphate (SP) is a monophosphate. The amount tested is always $R_A$=0.06 for gel 4c.

Thus, three crosslinked hyaluronic acid gels 3d, 4b and 4c comprising the use of sodium trimetaphosphate (STMP), sodium triphosphate (STPP) or sodium phosphate (SP) as compound A are prepared according to the abovementioned procedure.

Gel 3a, which is free of phosphate salt, is thus the control. It is also prepared according to the abovementioned procedure. Gels 3a and 3d are those of Example 2.

Table 7 below details the nature and amounts of the compounds used.

TABLE 7

| Parameters | A | $R_A$ | $R_{BDDE}$ | Crosslinking | [HA] (mg/g) | $\% \frac{HA_{non\text{-}crosslinked}}{HA_{non\text{-}crosslinked}\,+\,crosslinked}$ |
|---|---|---|---|---|---|---|
| 3a (comparative) | / | 0 | 0.04 | 72 hours at 21 ± 2° C. (BDDE + STMP) | 18 | 10% |
| 3d (invention) | STMP | 0.06 | | | | |
| 4b (invention) | STPP | 0.06 | | | | |
| 3d (invention) | SP | 0.06 | | | | |

The viscoelastic properties of gels 3a, 3d, 4b and 4c, measured according to the abovementioned protocols, are presented in Table 8 below.

TABLE 8

| | G' (Pa) | δ (°) | Compression strength (in N.s.) | Injection force (in N) |
|---|---|---|---|---|
| 3a (comparative) | 96 | 16.2 | 16.4 | 12.4 |
| 3d (invention) | 197 | 10.8 | 20.2 | 9.5 |
| 4b (invention) | 123 | 12.0 | 16.8 | 10.6 |
| 4c (invention) | 106 | 16.4 | 16.6 | 9.3 |

The mechanical properties of gels 4b and 4c remain better than those of the control gel 3a free of phosphate salt. STPP and SP thus also have an advantageous effect as regards the viscoelastic properties.

The degradation-resistance properties of gels 3a, 3d, 4b and 4c, measured according to the abovementioned protocols, are presented in Table 9 below.

TABLE 9

| | Loss of G' after sterilization (%) | Loss of G' after oxidative stress (%) |
|---|---|---|
| 3a (comparative) | 40 | 73 |
| 3d (invention) | 15 | 30 |
| 4b (invention) | 16 | 29 |
| 4c (invention) | 31 | 62 |

As for gel 3d crosslinked in the presence of STMP, the degradation resistance is improved for gels 4d crosslinked in the presence of STPP, and for gel 4c crosslinked in the presence of SP.

The use of STPP or SP in the presence of BDDE in the crosslinking medium also makes it possible to obtain an advantageous effect on the mechanical properties. The degradation resistance is also improved with the use of these phosphate salts STPP and SP.

Example 4: Demonstration of a Synergistic Effect of a Phosphate Salt (STMP) Used During Crosslinking with BDDE Four crosslinked hyaluronic acid gels 5a, 5b, 5c and 5d, comprising the use of BDDE and STMP as compound A, are prepared according to the abovementioned procedure.

Gel 5a is in accordance with the present invention since it is obtained after a step of crosslinking in the simultaneous presence of BDDE and STMP.

Gels 5b, 5c and 5d are not in accordance with the present invention since they are obtained after a dissociated crosslinking step. Specifically, the BDDE and STMP were integrated sequentially and with a significant time interval with regard to the crosslinking.

Table 10 below details the nature and amounts of compounds used.

TABLE 10

| Parameters | $R_A$ | $R_{BDDE}$ | Crosslinking at 21 ± 2° C. | [HA], mg/g | $\% \frac{HA_{non\text{-}crosslinked}}{HA_{non\text{-}crosslinked}\,+\,crosslinked}$ |
|---|---|---|---|---|---|
| 5a (invention) | 0.06 | 0.04 | 72 hours STMP + BDDE | 18 | 0 |
| 5b (comparative) | | | 72 hours STMP then 72 hours BDDE | | |
| 5c (comparative) | | | 24 hours STMP then 72 hours BDDE | | |
| 5d (comparative) | | | 72 hours BDDE then STMP added post-crosslinking | | |

The viscoelastic properties of gels 5a, 5b, 5c and 5d, measured according to the abovementioned protocols, are presented in Table 11 below.

TABLE 11

| | G' (Pa) | δ (°) | Compression strength (N.s.) | Injection force (N) |
|---|---|---|---|---|
| 5a (invention) | 136 | 9.6 | 22.6 | 38.0 |
| 5b (comparative) | 17 | 18.5 | 3.2 | 11.5 |
| 5c (comparative) | 87 | 13.5 | 17.7 | 31.8 |
| 5d (comparative) | 76 | 13.7 | 17.8 | 34.9 |

Gel 5a in accordance with the invention has optimum rheological properties, by virtue of crosslinking performed with BDDE in the presence of STMP.

If the same amount of STMP is incorporated after crosslinking with BDDE, the effect on the mechanical properties is no longer observed: thus, gel 5d has significantly lower mechanical properties.

Additionally, there is no improvement in the mechanical properties of the gel if STMP is incorporated into the HA 24 hours before the addition of BDDE (gel 5c), and there is even degradation of the mechanical properties of the gel if STMP is added 72 hours before the addition of BDDE (gel 5b).

In other words, these results demonstrate that the effect of the reaction {STMP+BDDE} is not equivalent to {STMP}+{BDDE}; there is thus a synergistic effect when the crosslinking reaction of HA is performed via a non-dissociated combination between the BDDE and STMP.

Example 5: Effect of STMP with Faster Crosslinking Conditions

Three crosslinked hyaluronic acid gels 6a, 6b and 6c comprising the use of BDDE alone (i.e. 6a) or with STMP as compound A (i.e. 6b and 6c) are prepared according to the abovementioned procedure.

Table 12 below details the nature and amounts of the compounds used.

TABLE 12

| Parameters | $R_A$ | $R_{BDDE}$ | Crosslinking | [HA], mg/g | % $\frac{HA_{non\text{-}crosslinked}}{HA_{non\text{-}crosslinked\ +\ crosslinked}}$ |
|---|---|---|---|---|---|
| 6a (comparative) | 0 | 0.15 | 3 hours at 52 ± 2° C. (BDDE + STMP) | 20 | 10% |
| 6b (invention) | 0.06 | | | | |
| 6c (invention) | 0.15 | | | | |

This mode of heat-mediated crosslinking (52° C.) is interesting in that it is faster than at room temperature.

The viscoelastic properties of gels 6a, 6b and 6c, measured according to the abovementioned protocols, are presented in Table 13 below.

TABLE 13

| | G' (Pa) | δ (°) | Compression strength (N.s.) | Injection force (N) |
|---|---|---|---|---|
| 6a (comparative) | 217 | 10.5 | 18.1 | 10.1 |
| 6b (invention) | 299 | 10.2 | 19.0 | 11.1 |
| 6c (invention) | 426 | 9.5 | 18.9 | 10.2 |

In this case also, an increase in the elastic modulus G' is observed when the crosslinking is performed in the presence of the phosphate salt (STMP).

Example 6: Comparison STMP vs NaCl

Four hyaluronic acid crosslinked gels 7a, 7b, 7c and 7d comprising the use of BDDE alone (i.e. 7a), with STMP as compound A (i.e. 7b), or with NaCl as compound A (i.e. 7c and 7d), were prepared according to the above protocol.

Gel 7a is devoid of any STMP and NaCl and is therefore the reference.

TABLE 14

| Parameters | A | $R_A$ | $R_{BDDE}$ | Crosslinking | [HA], mg/g | % $\frac{HA_{non\text{-}crosslinked}}{HA_{non\text{-}crosslinked\ +\ crosslinked}}$ |
|---|---|---|---|---|---|---|
| 7a (reference) | / | 0 | 0.02 | 72 H at 21 ± 2° C. (BDDE + A) | 23 | 10% |
| 7b (invention) | STMP | 0.06 | | | | |
| 7c (comparative) | NaCl | 0.18 | | | | |
| 7d (comparative) | NaCl | 1.5 | | | | |

Since SMTP is a trivalent salt and NaCl a monovalent salt, gel 7c was made with an amount of NaCl corresponding to 3 times that of the gel 7b. Gel 7d is manufactured with a greater amount of NaCl ($R_A$=1.5), corresponding to a massic concentration of NaCl in the crosslinking medium of 3%, as described in FR 2 997 085.

The viscoelastic properties of gels 7a, 7b, 7c et 7d, measured according to the above described protocols, are given in Table 15.

TABLE 15

| | G' (in Pa) | δ (in °) | Compression strength (N.s.) | Injection force (N) |
|---|---|---|---|---|
| 7a (reference) | 14 | 50.9 | 3.1 | 10.3 |
| 7b (invention) | 49 | 33.9 | 10.3 | 14.0 |

TABLE 15-continued

| | G' (in Pa) | δ (in °) | Compression strength (N.s.) | Injection force (N) |
|---|---|---|---|---|
| 7c (comparative) | 23 | 45.7 | 3.2 | 9.4 |
| 7d (comparative) | 6.3 | 63.0 | 1.1 | 8.3 |

Contrary to gel 7b according to the invention, reference gel 7a and comparative gels 7c and 7d are not suitable for filling wrinkles because their phase angle δ is greater than 45°.

The invention claimed is:

1. A process for preparing a crosslinked gel of at least one polysaccharide or a salt thereof, comprising:
   a) providing a solution formed from an aqueous medium comprising at least one polysaccharide or a salt thereof in a non-crosslinked form, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate;
   b) crosslinking the solution from step a) to form a crosslinked gel, and
   c) recovering said crosslinked gel.

2. The process according to claim 1, further comprising homogenizing the solution from step a), prior to and/or simultaneously with the crosslinking step b).

3. The process according to claim 1, wherein the crosslinking step b) is performed at a temperature from 15 to 35° C.

4. The process according to claim 1, wherein the crosslinking step b) is performed over a period of between 5 hours and 336 hours.

5. The process according to claim 1, wherein the difunctional or multifunctional epoxide crosslinking agent is butanediol diglycidyl ether.

6. The process according to claim 1, wherein the polysaccharide is hyaluronic acid or a salt thereof.

7. The process according to claim 6, wherein the hyaluronic acid salt is chosen from a sodium salt, a potassium salt, a zinc salt, a silver salt, and mixtures thereof.

8. The process according to claim 1, wherein the solution from step a) comprises a number of moles of phosphate salt(s)/total number of moles of polysaccharide units molar ratio of between 0.005 and 1.

9. The process according to claim 1, wherein the solution from step a) comprises a number of moles of difunctional or multifunctional epoxide crosslinking agent(s)/total number of moles of polysaccharide units molar ratio of between 0.005 and 1.

10. The process according to claim 1, further comprising adding at least one non-crosslinked polysaccharide after step b) but prior to, simultaneously with or subsequent to the recovery of step c).

11. The process according to claim 1, wherein the crosslinked polysaccharide(s) included in the crosslinked gel have a degree of modification of between 0.1% and 10%.

12. The process according to claim 1, wherein the crosslinked gel has an elastic modulus (G') of between 20 and 1000 Pa associated with a phase angle (δ) of less than 45°.

13. An injectable and sterile dermatological composition comprising, in a physiologically acceptable medium, at least one crosslinked gel having at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

14. A cosmetic or dermatological composition comprising at least one crosslinked gel having at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

15. A kit comprising:
packaging containing at least one dose of a crosslinked gel, the crosslinked gel having at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate; and
a device for injection into or through the skin or a skin microperforation device for administration of the one dose of the crosslinked gel.

16. A method for filling skin volume defects by administering a crosslinked gel having at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

17. A crosslinked gel for treating gingival deficiencies comprising at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

18. A crosslinked gel for articular viscosupplementation comprising at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

19. A crosslinked gel for treating ophthalmic disorders comprising at least one polysaccharide or a salt thereof, at least one difunctional or multifunctional epoxide crosslinking agent chosen from butanediol diglycidyl ether, diepoxyoctane, 1,2-bis(2,3-epoxypropyl)-2,3-ethylene, and mixtures thereof, and at least one phosphate salt, the at least one phosphate salt being sodium trimetaphosphate.

* * * * *